(12) United States Patent
Jeon et al.

(10) Patent No.: US 11,109,959 B2
(45) Date of Patent: Sep. 7, 2021

(54) INTRAOCULAR LENS AND METHOD OF MANUFACTURING THE SAME

(71) Applicants: KOREA INSTITUTE OF SCIENCE AND TECHNOLOGY, Seoul (KR); THE CATHOLIC UNIVERSITY OF KOREA INDUSTRY-ACADEMIC COOPERATION FOUNDATION, Seoul (KR)

(72) Inventors: Ho Jeong Jeon, Seoul (KR); Myoung Ryul Ok, Seoul (KR); Yu Chan Kim, Seoul (KR); Hyun Kwang Seok, Seoul (KR); Choun Ki Joo, Seoul (KR); Byoung Chan Choi, Gwangmyeong-si (KR)

(73) Assignees: KOREA INSTITUTE OF SCIENCE AND TECHNOLOGY, Seoul (KR); THE CATHOLIC UNIVERSITY OF KOREA INDUSTRY-ACADEMIC COOPERATION FOUNDATION, Seoul (KR)

(*) Notice: Subject to any disclaimer, the term of this patent is extended or adjusted under 35 U.S.C. 154(b) by 78 days.

(21) Appl. No.: 16/512,400

(22) Filed: Jul. 16, 2019

(65) Prior Publication Data

US 2020/0015961 A1    Jan. 16, 2020

(30) Foreign Application Priority Data

Jul. 16, 2018    (KR) .................... 10-2018-0082504

(51) Int. Cl.
*A61F 2/16*    (2006.01)

(52) U.S. Cl.
CPC .......... *A61F 2/1613* (2013.01); *A61F 2/1694* (2013.01); *A61F 2/1601* (2015.04);
(Continued)

(58) Field of Classification Search
CPC .................. A61F 2/1613; A61F 2/1659; A61F 2002/1696; A61F 2/16; A61F 2002/1699;
(Continued)

(56) References Cited

U.S. PATENT DOCUMENTS

2016/0095698 A1* 4/2016 Jeon ..................... A61F 2/16
                                                    623/6.43

FOREIGN PATENT DOCUMENTS

JP      5778855 B2    9/2015
KR   20010018345 A    3/2001
(Continued)

OTHER PUBLICATIONS

Korean Office Action for KR Application No. 10-2018-0082504 dated Feb. 18, 2020.

*Primary Examiner* — Javier G Blanco
(74) *Attorney, Agent, or Firm* — Cantor Colburn LLP

(57) ABSTRACT

There is provided an intraocular lens including an optic portion having a circular shape from one side thereof and including a first pattern which includes a ridge and a groove, and a plurality of haptic portions extending from an outer circumferential edge of the optic portion and each including a second pattern which includes a ridge and a groove, in which at least one of the ridges included in the first pattern and the second pattern and at least one of the grooves included in the first pattern and the second pattern includes a section in which a width is formed differently.

8 Claims, 12 Drawing Sheets

(52) U.S. Cl.
CPC ..... *A61F 2/1659* (2013.01); *A61F 2002/1681* (2013.01); *A61F 2002/1696* (2015.04); *A61F 2240/001* (2013.01); *A61L 2430/16* (2013.01)

(58) Field of Classification Search
CPC ........ A61F 2002/1681; A61F 2002/009; A61F 2250/0026; A61F 2250/0051; A61F 2/0077
See application file for complete search history.

(56) References Cited

FOREIGN PATENT DOCUMENTS

| | | | | |
|---|---|---|---|---|
| KR | 1020110020300 A | 3/2011 | | |
| KR | 1020160040807 A | 4/2016 | | |
| KR | 1020170036056 A | 3/2017 | | |
| WO | WO-2016022933 A1 * | 2/2016 | ................ | F16L 9/12 |

* cited by examiner

INTRAOCULAR LENS AND METHOD OF MANUFACTURING THE SAME

CROSS-REFERENCE TO RELATED PATENT APPLICATION

This application claims the benefit of Korean Patent Application No. 10-2018-0082504, filed on Jul. 16, 2018, in the Korean Intellectual Property Office, the disclosure of which is incorporated herein in its entirety by reference.

BACKGROUND

Field

The present invention relates to an intraocular lens and a method of manufacturing the same.

Description of the Related Art

In general, a human eye is similar to structure and function of a camera. A lens having a convex lens-shaped transparent structure is provided at a rear of a pupil to function as a camera lens. If the lens becomes opaque due to damage from the outside or due to unnecessary abuse of eye drops, radioactivity, exposure to various harmful electromagnetic waves, and the like, a cataract may be induced. As one of the surgical methods for treating the cataract, a method of implanting an intraocular lens that can replace the function of the lens has been used. In this case, an operation has been made to insert most of the intraocular lenses into an inside of a part called a capsular bag within an eyeball or into a space between the capsule bag and an iris. However, opacity is likely to recur due to proliferation of cells that lead to an after cataract and migration of cells to the intraocular lens side, even after the operation. Therefore, there is a need for a technology capable of retarding or inhibiting the proliferation and migration of cells and the like that induce the after cataract.

RELATED ART DOCUMENT

Patent Document (Patent Document 1) Korean Patent Laid-Open Publication No. 2001-0018345 (Mar. 5, 2001)

SUMMARY

An object of an embodiment of the present invention provides an intraocular lens which forms information regarding a predetermined width or the like in a pattern formed on the intraocular lens within a specific range to control a speed and a direction of a cell passing through the pattern to thereby prevent eye diseases such as an after cataract from recurring.

An object of an embodiment of the present invention provides an intraocular lens which forms information regarding a predetermined width or the like of a pattern formed on the intraocular lens within a specific range of micro units, increases surface roughness through a structure, which is formed within a range of nano units, within the formed pattern to hinder mobility of cells.

An object of an embodiment of the present invention provides an intraocular lens capable of migrating cells in one direction by forming a boundary portion where mobility of cells is hindered within a pattern formed on an intraocular lens.

In accordance with one aspect of the present invention, an intraocular lens includes: an optic portion having a circular shape from one side thereof and including a first pattern which includes a ridge and a groove, and a plurality of haptic portions extending from an outer circumferential edge of the optic portion and each including a second pattern which includes a ridge and a groove, in which at least one of the ridges included in the first pattern and the second pattern and at least one of the grooves included in the first pattern and the second pattern includes a section in which a width is formed differently.

A width ratio of the ridge and the groove included in the first pattern and the second pattern may be formed within a range of 1:2 to 1:8.

A pattern in which the width of the ridge may be 5 micrometers and the width of the groove is 30 micrometers may be included in at least some section of the whole pattern.

The pattern may be formed over the haptic portion and the optic portion, the width of the ridge may be 5 micrometers and the width of the groove is different in each section, and the width of the groove formed on the haptic portion may be formed to be wider than that of the groove formed on the optic portion.

The pattern may be formed over a front surface part and a rear surface part of the optic portion and a front surface part and a rear surface part of the haptic portion which are located at a front side with respect to a direction in which light passes through the optic portion, and the pattern may be formed on the front surface part and the rear surface part and may be formed to continuously extend through a side part over the front surface part and the rear surface part.

The groove may include a rugged part of nanometer units formed on a surface thereof.

The groove may include a boundary portion which retards or blocks migration of a cell.

The boundary portion may form a plurality of cell migration paths within the width of the groove to change a migration speed of a cell.

The boundary portion may obliquely extend inward from a side wall of the groove to narrow a cross sectional area through which the cell passes in a forward direction in which the cell migrates and may block the migration of the cell in a reverse direction to guide the migration direction of the cell.

The boundary portion may be formed to protrude upward from a bottom surface of the groove and may obliquely extend to bypass and block the migration of the cell in a forward direction in which the cell migrates and may increase the cross sectional area through which the cell passes in a reverse direction.

In accordance with another aspect of the present invention, a method of manufacturing an intraocular lens includes: seating a workpiece including a haptic portion having a circular shape from one side thereof and one or more optic portion extending from an outer circumferential edge of the haptic portion; irradiating a micro-sized laser beam to the haptic portion and the optic portion to process a predetermined pattern to which a cell is guided; increasing surface roughness of a groove included in a predetermined pattern by forming a structure having the nano-sized surface roughness in the predetermined pattern formed by the micro-sized laser beam; and forming the predetermined pattern so that a width of the groove in the first pattern formed on the optic portion is narrower than that of the groove in the second pattern formed on at least a part of the haptic portion and forming the predetermined pattern to be guided to the outer circumferential edge of the haptic portion or the optic portion so that the cell is away from a center of the optic portion.

An embodiment of the present invention may provide an intraocular lens which forms information regarding a predetermined width or the like in a pattern formed on the intraocular lens within a specific range to control a speed and a direction of cells passing through the pattern to thereby prevent eye diseases such as an after cataract from recurring.

An embodiment of the present invention may provide an intraocular lens which forms information regarding a predetermined width or the like of a pattern formed on the intraocular lens within a specific range of micro units, increases surface roughness through a structure, which is formed within a range of nano units, within the formed pattern to hinder mobility of cells.

An embodiment of the present invention may provide an intraocular lens capable of migrating cells in one direction by forming a boundary portion where mobility of cells is hindered within a pattern formed on an intraocular lens.

DETAILED DESCRIPTION

Hereinafter, embodiments of the present invention will be described with reference to the accompanying drawings. However, the embodiments are described by way of examples only and the present invention is not limited thereto.

In describing the present invention, when a detailed description of well-known technology relating to the present invention may unnecessarily make unclear the spirit of the present invention, a detailed description thereof will be omitted. Further, the following terminologies are defined in consideration of the functions in the present invention and may be construed in different ways by the intention of users and operators. Therefore, the definitions thereof should be construed based on the contents throughout the specification.

As a result, the spirit of the present invention is determined by the claims and the following embodiments may be provided to efficiently describe the spirit of the present invention to those skilled in the art.

Figure 1:
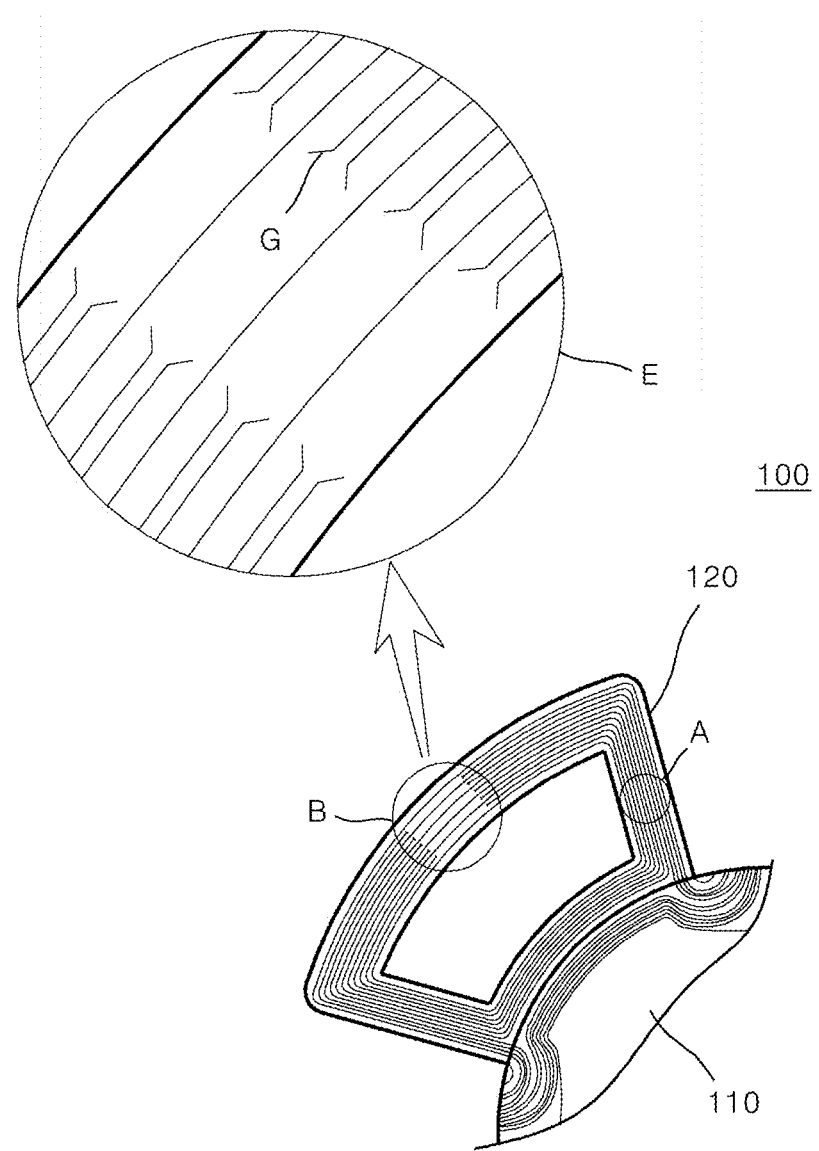
FIG. 1 is a diagram showing an intraocular lens according to an embodiment of the present invention.
Figure 2:
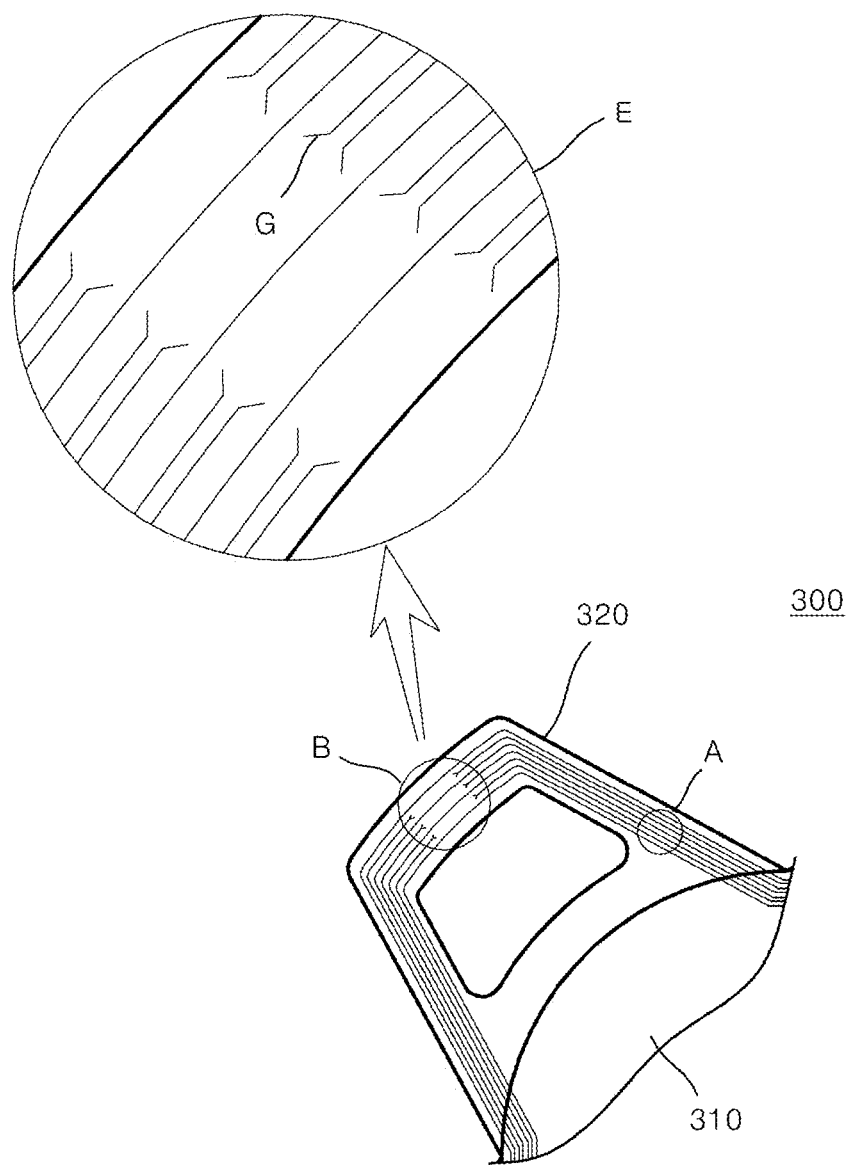
FIG. 2 is a diagram showing an intraocular lens according to other embodiments of the present invention.

In FIGS. 1 and 2, intraocular lenses 100 and 300 are displayed through a display area E in which patterns A and B are formed, which may be applied to the respective symmetrical area of the following intraocular lenses 100, 200, 300, and 400.

In addition, a first pattern A for describing the present invention may be formed on at least optic portions 110, 210, 310, and 410, and may be provided over the haptic portions 120, 220, 320, and 420. Meanwhile, a second pattern B may be formed on the haptic portions 120, 220, 320, and 420. Functions of the first pattern A and the second pattern B on the intraocular lenses 100, 200, 300, and 400 and respective differences in the functions will be described in detail below.

FIG. 1 is a diagram illustrating the intraocular lens 100 according to an embodiment of the present invention.

Referring to FIG. 1, the intraocular lens 100 may include the optic portion 110 and the haptic portion 120. The patterns A and B may be formed on the optic portion 110 and the haptic portion 120. The patterns A and B may be classified into a first pattern A and a second pattern B or the like according to a formed position or information on the pattern dimension. Here, the dimension information may be information including the sizes of ridges 11 and 12 (FIGS. 3A and 3B) and grooves 21 and 22 (FIGS. 3A and 3B) included in the patterns A and B.

In detail, the dimension information may be depths D1 and D2 (FIGS. 3A and 3B) and widths G1 and G2 (FIGS. 3A and 3B) of the groove, heights D1 and D2 (FIGS. 3A and 3B) and widths R1 and R2 (FIGS. 3A and 3B) of the ridge, and the like. The dimension information may be described below with reference to FIGS. 3A and 3B.

On the other hand, when the optic portion 110 capable of transmitting light and having a circular shape from one side thereof is implanted into a human body, since light is incident through the optic portion 110, foreign matters may be prevented from being located on the optic portion 110. Here, foreign matters may be epithelial cells that cause eye disease such as an after cataract. For example, an opaque lens may be removed from a cataract patient and the intraocular lens 100 may be implanted. After the implantation, the intraocular lens may become opaque again by the ocular epithelial cells which cause a small amount of after cataracts remaining in the human body. To prevent this, the patterned intraocular lens 100 may be implanted to retard or block migration or proliferation of cells on a surface of the intraocular lens 100.

As shown in FIG. 1, the intraocular lens 100 of the present invention may be provided with the patterns A and B from the vicinity of an edge of the optic portion 110 to the haptic portion 120. The vicinity of the edge means a range extending from an outer circumferential edge of the optic portion 110 on the optic portion 110 so as to bypass the cell so that a cell is away from a center of the optic portion 110. As described above, the patterns A and B may not be formed by a predetermined distance in a radial direction from the center of the optic portion 110 which is an area of the optic portion 110 excluding the vicinity. The patterns A and B may serve to guide residual cells to be away from the center of the optic portion 110 or inhibit the proliferation of foreign matters (for example, epithelial cells) so that the residual cells do not migrate onto the area of the optic portion 110 capable of transmitting light.

FIG. 2 is a diagram showing the intraocular lens 300 according to another embodiment of the present invention.

Describing the difference from FIG. 1 with reference to FIG. 2, the first pattern A may be formed so that a width G1 of the groove is narrower than a width G2 of the groove of the second pattern B. For example, a width R1 of the ridge may be 5 micrometers and the width G1 of the groove may be 10 to 20 micrometers. In the present example, the first pattern A may be formed to guide cells migrating from the haptic portion 320 toward the optic portion 310 in a direction away from the center of the optic portion 310 again. The second pattern B can more widen a width G2 of the groove than the first pattern A so as to lower the mobility of cells. For example, the width of the ridge 12 may be 5 micrometers, and the width of the groove 22 may be 30 micrometers. The direction may be a direction that is located on the haptic portion 320 and away from the center of the optic portion 310.

Here, the second pattern B may be located on the haptic portion 320. Even the haptic portion 320 may be formed in a portion formed around the optic portion 310 in an arc shape. For example, in the case of the entire part of the arc or when an arc is divided into three sections in a circumferential direction, the haptic portion 320 may be formed in one of the three sections. The examples of FIGS. 1 and 2 show a case where the second pattern B is formed in the middle section of the three sections, and may also be formed on the haptic portion 320 except for this example.

In other words, a speed at which a cell migrates toward the center of the optic portion 310 is retarded, and a cell adjacent to the optic portion 310 may migrate faster than a speed at which a cell migrates toward the center of the optic portion 310 in the direction away from the haptic portion 320 or the optic portion 310. The migration speed of cells may be reduced by the structure formed in the nano unit on the surface of the pattern formed in the micro unit, the migration speed may be increased or decreased according to whether the cell migrates along a side wall of the ridge while coming into contact with the ridge included in the pattern, and the migration speed of cells may be determined differently due to biological factors of cells.

Here, an example in which the nano-sized surface structure formed on the surface of the pattern can hinder the migration of cells to control the migration speed of cells will be described below. Of course, it is possible to expect an effect of blocking the migration of cells along the side wall by making it difficult for the cell to migrate toward the side wall of the ridge due to the nano-sized structure. In addition to this effect, the width G2 of the groove may be formed to be wider to allow more cells to migrate through a bottom surface, such that a surface of at least one of the optic portion 310 and the haptic portion 320 may be selectively formed to hinder the migration so as to hinder the migration due to the nano-sized structure formed on the bottom surface.

Meanwhile, according to the embodiments of the present invention, locations at which the patterns A and B are formed may be as follows. The second pattern B may be formed within a part of the haptic portions 120 and 320, and for example, may be formed within a ⅓ section of the haptic portions 120 and 320 in the radial direction from the furthest point from the center of the optic portions 110 and 310. Alternatively, the second pattern B may be located at a portion extending in a direction parallel to the outer circumferential edges of the optic portions 110 and 310 in the haptic portions 120 and 320. As described above, FIG. 2 shows that the extending direction in which the pattern A and B are formed may determine the progress direction of cells to determine the migration and growth direction of cells, and the dimension information of the patterns A and B may be information that can serve as a guide to determine the mobility of cells including the migration speed of cells. These contents will be described below in detail with reference to FIGS. 3 to 8.

Figure 3A:
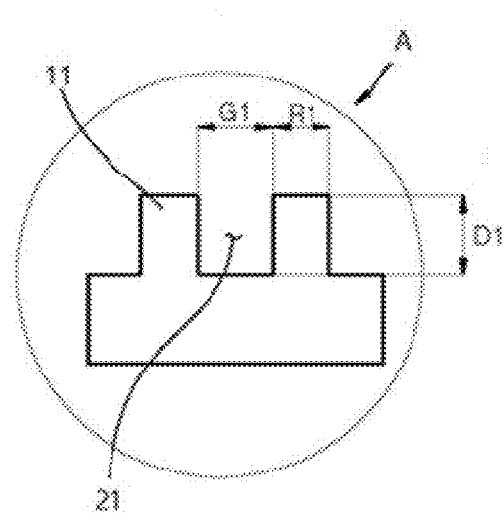
FIG. 3A is a diagram showing a cross section of a first pattern according to an embodiment of the present invention.
Figure 3B:
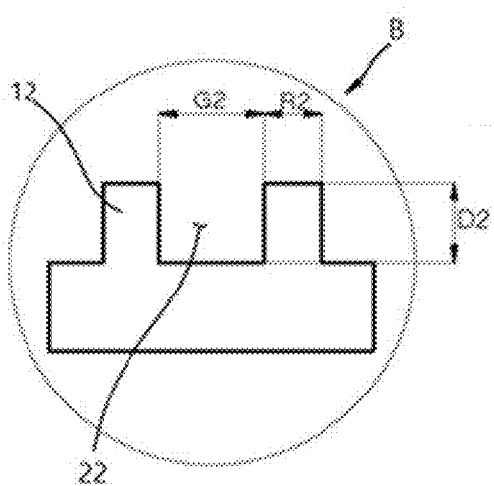
FIG. 3B is a diagram showing a cross section of a second pattern according to an embodiment of the present invention.

FIG. 3A is a diagram showing a cross section of the first pattern A of the present embodiment, and FIG. 3B is a diagram showing a cross section of the second pattern B of the present embodiment.

Referring to FIGS. 3A and 3B, the first pattern A and the second pattern B may be classified according to their respective locations as described above, and may vary according to the dimension information. For example, the first pattern A located on the optic portion 110 side may be formed to be larger than the second pattern B located on the haptic portion 120 side. More specifically, the width G1 of the groove included in the first pattern A may be formed to be narrower than the width G2 of the groove included in the second pattern B.

As an example, the width G1 of the groove included in the first pattern A may be formed within a range of 5 to 30 micrometers. The wider the width (G1) of the groove within the above range, the lower the mobility of cells, and the narrower the width (G1) of the groove within the above range, the higher the mobility of cells. However, the case where the groove is formed at a width equal to or less than the dimension of cells in consideration of the dimension of cells may act as an obstacle to the mobility. More specifically, the width G1 of the groove included in the first pattern A may be 10 micrometers and the width G2 of the groove included in the second pattern B may be 30 micrometers. A numerical value of this width may be a numerical value determined by a test of the mobility of cells under the same conditions through a plurality of patterns formed with different numerical values.

Figure 7A:
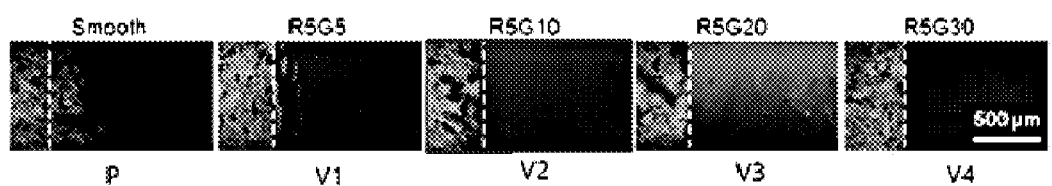
FIG. 7A is a graph showing mobility of cells according to a pattern dimension of an embodiment of the present invention.
Figure 7B:
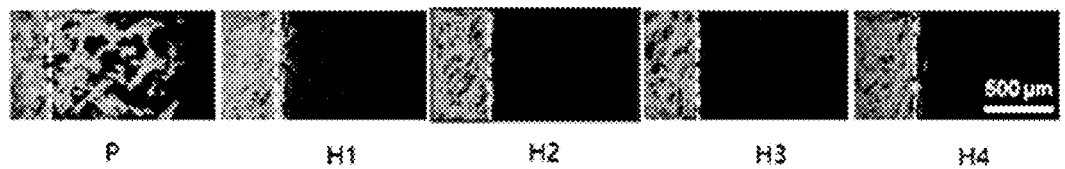
FIG. 7B is a graph showing mobility of cells according to a pattern dimension of an embodiment of the present invention.

Meanwhile, referring to FIGS. 7A and 7B showing the test results of cells migration inhibition rate, in FIG. 7A, P is arranged so that a cultured cell group migrates in a plane, and V1 to V4 are arranged so that cells migrate in a direction of traversing the ridges 11 and 12 and the grooves 21 and 22 included in the patterns A and B. Here, the widths R1 and R2 of the ridges are set to be equal to 5 micrometers, and experimental groups in which the widths G1 and G2 of the grooves are changed are compared with each other.

If the above test group is maintained for a certain period of time, the degree of cell migration may be confirmed. For example, in the case of FIG. 7B, cells are kept in the above experimental state for about 5 days, and the cell migration inhibition rate may be confirmed by comparing the cell migration with the time before the passage of time. As the result of confirming the cell migration inhibition rate based on the present experiment, in the case where the grooves 21 and 22 are 10 micrometers, the inhibition rate is highest. In one experiment, the inhibition rate of cells migrating on the plane was 0%, the migration distance was 800 micrometers, the inhibition rate was 87.5% and the migration distance was 100 micrometers when the grooves 21 and 22 were 5 micrometers, the inhibition rate was 98.75% and the migration distance was 10 micrometers when the grooves 21 and 22 are 10 micrometers, the inhibition rate was 97.5% and the migration distance was 20 micrometers when the grooves 21 and 22 are 20 micrometers, and the inhibition rate was 96.25% and the migration distance was 30 micrometers when the grooves 21 and 22 are 30 micrometers. Experimental results are obtained when the widths of ridges 11 and 12 of the experiment were equally prepared at 5 micrometers and cells were left under the same condition for 5 days.

Meanwhile, apart from the above-mentioned experiment results, the migration of cells migrating along the groove is the largest and active when the widths G1 and G2 of the grooves are 20 micrometers, and in the case of V4, the migration of cells migrating along the groove is the lowest when the widths G1 and G2 of the grooves are 30 micrometers. Basically, according to the result under the assumption that the cell may be guided in the intended direction, the case of P having lower mobility or the case where the cell crosses the ridges 11 and 12 may be excluded.

Based on the above experimental results, it is possible to create an environment in which cells migrate. Basically, the environment may include retarding or blocking the migration and proliferation of cells which are progressed in the optic portion 110, but may further include promoting the progress of cells to quickly migrate cells, which migrate from the haptic portion 120 toward the optic portion 110, toward the outer circumferential edges of the haptic portion 120 or the optic portion 110 again. Therefore, the embodiments of the present invention may be selectively adopt the structure of the patterns A and B in which the differential speed of cells appear according to the section in which cells are located, so as to control the migration of cells.

In the embodiment of FIG. 1, each of the patterns A and B is provided at a location (location in the vicinity of the edge spaced apart from the central point of the optic portion 110) adjacent to the optic portion 110 including the outer circumferential edge of the optic portion 110 which is a location of the first pattern A and is provided at a location spaced apart from the haptic portion 120, that is, the optic portion 110 which is a location of the second pattern B.

As described above, the patterns A and B may be provided in different forms in order to accomplish the above object. These embodiments will be described below with reference to FIGS. 4A and 4B.

Figure 4A:
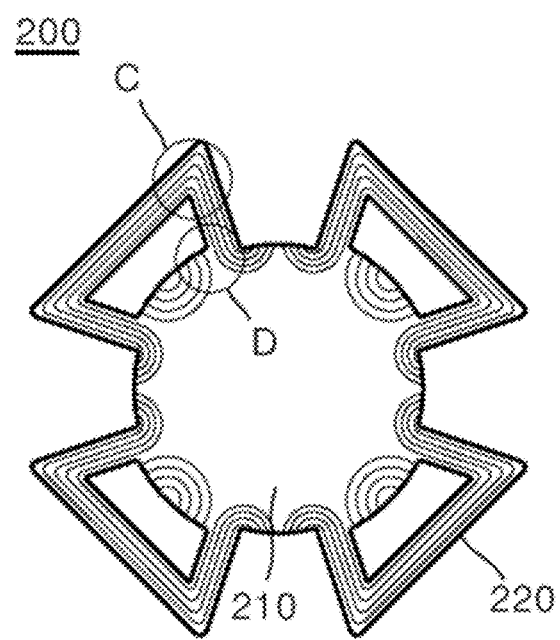
FIG. 4A is a diagram showing an example of a pattern formed on an intraocular lens according to another embodiment of the present invention.
Figure 4B:
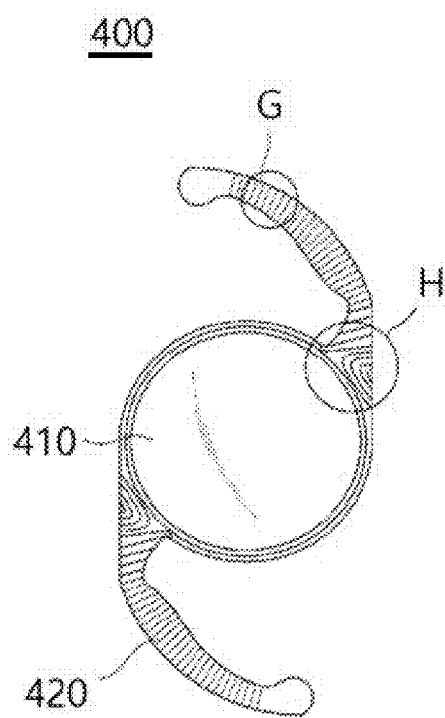
FIG. 4B is a diagram showing an example of a pattern formed on an intraocular lens according to another embodiment of the present invention.

FIGS. 4A and 4B are diagrams showing an example of the patterns A and B formed on the intraocular lens 100 according to another embodiment of the present invention.

Referring to FIG. 4A, the first pattern A may be formed so that the width G1 of the groove is narrower than the width G2 of the groove of the second pattern B. For example, the width R1 of the ridge may be 5 micrometers and the width G1 of the groove may be 10 to 20 micrometers. In the present example, the first pattern A may be formed to be again guided in the direction in which cells migrating from the haptic portion 220 toward the optic portion 210 are away from the optic portion 210 in the portion where the first pattern A is formed. The second pattern B can more widen the width G2 of the groove than the first pattern A so as to lower the mobility of cells. For example, the width of the ridge 12 may be 5 micrometers, and the width of the groove 22 may be 30 micrometers.

In addition, the patterns A and B formed on the haptic portion 220 may extend on the same line and extend to the optic portion 210, but the pattern A formed on the optic portion 210 may not be connected to the haptic portion 220 and may be independently formed in a closed curve shape. The closed curve shape may be formed to be connected to the back surface through the side surface from the front surface based on a direction in which light passes through the optic portion 210.

In other words, the structure of the patterns A and B may retard the speed at which cells migrate toward the center of the optic portion 210, and cells already adjacent to the optic portion 210 may migrate faster than the speed at which cells migrates toward the center of the optic portion 210 in the direction away from the haptic portion 220 or the optic portion 210.

Referring to FIG. 4B, the first pattern A may be formed so that the width G1 of the groove is narrower than the width G2 of the groove of the second pattern B. For example, the width R1 of the ridge may be 5 micrometers and the width G1 of the groove may be 10 to 20 micrometers. In the present example, the first pattern A may be formed to be again guided in the direction in which cells migrating from the haptic portion 420 toward the optic portion 410 are away from the optic portion 410 in the portion where the first pattern A is formed. The second pattern B can more widen the width G2 of the groove than the first pattern A so as to lower the mobility of cells. For example, the width of the ridge 12 may be 5 micrometers, and the width of the groove 22 may be 30 micrometers.

In addition, the patterns A and B formed on the haptic portion 420 may extend on the same line and extend to the optic portion 410, but the pattern A formed on the optic portion 410 may not be connected to the haptic portion 420 and may be independently formed in a closed curve shape. The closed curve shape may be formed to be connected to the back surface through the side surface from the front surface based on a direction in which light passes through the optic portion 410.

In other words, the speed at which a cell migrates toward the center of the optic portion 410 is retarded, and a cell already adjacent to the optic portion 410 may migrate faster than the speed at which a cell migrates toward the center of the optic portion 410 in the direction away from the haptic portion 420 or the optic portion 410.

Figure 5:
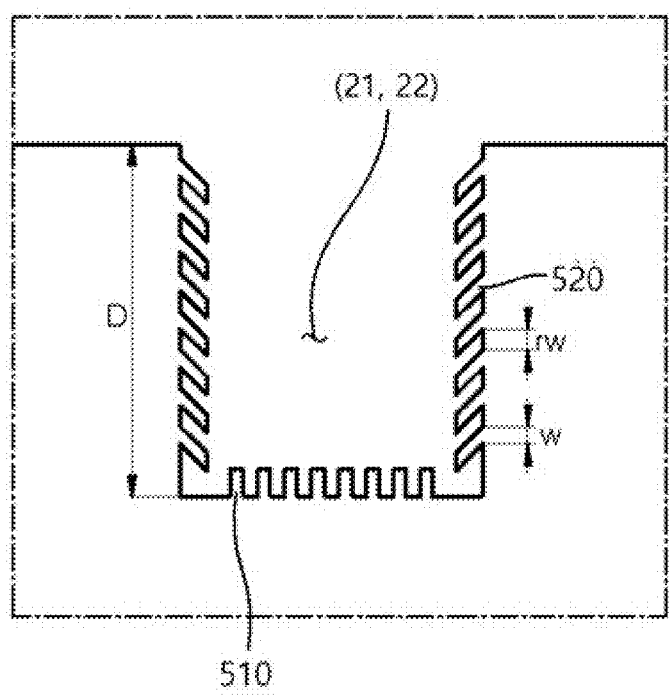
FIG. 5 is a diagram showing a structure of nano units formed on a groove according to an embodiment of the present invention.

FIG. 5 is a diagram showing a structure of nano units formed on the grooves 21 and 22 according to an embodiment of the present invention.

Referring to FIG. 5, the nano unit structure is formed on the surfaces of the grooves 21 and 22, and processing projections 510 and 520 may be provided. The processing projections 510 and 520 may be formed in units of nanometers and may have a structure for retarding or inhibiting the migration of cells. For example, the nano-sized processing projections 510 and 520 may be formed to extend in an oblique direction from the surfaces of the grooves 21 and 22.

In particular, the side processing projection 520 may be in a liquid state by being partly dissolved during the processing of the intraocular lens 100 by laser, and therefore, a part of the side processing projections 520 can sag in a downward direction due to the influence of self weight or viscosity for the predetermined time until being cured. That is, the sagging may include a downward (self weight) deformation due to the viscosity and the self weight in the liquid state at the time of dissolution. Accordingly, the processing projections 510 and 520 may be inclined at a certain angle downward direction for a period of time in which the dissolved state is maintained. Here, the downward direction is an example, and it may be changed by setting downward direction in the laser processing, and then the direction facing the progress direction of the cell may be the downward direction.

Therefore, when cured in the direction opposite to the migration direction of cells, the processing projections become factors inhibiting the mobility of cells, thereby inhibiting the mobility of cells. It goes without saying that the present invention is applied not only to the side processing projections 520 but also to the processing projections 510 formed on the bottom surface.

A projection interval rw may be formed in a range of 0.1 μm to 10 μm. When the projection interval rw is less than 0.1 μm, the roughness of the processing projections 510 and 520 is reduced and the inhibition against the mobility of cells is reduced, and when the projection interval rw exceeds 10 μm, the number of processing projections 520 is reduced to reduce the inhibition against the mobility of cells. As a result, the projection interval rw may be formed in a range of 0.1 μm to 10 μm.

In addition, a width w between adjacent processing projections 510 and 520 may be formed in the range of 0.1 μm to 10 μm. When the projection width w is less than 0.1 μm, the length that can extend from the surfaces of the grooves 21 and 22 is short, making it difficult to perform the function of inhibiting the migration of the cells, and when the projection width w exceeds 10 μm, the number of processing projections 520 that may be provided in a processing groove 101 is reduced, thereby making it difficult to secure a bonding force. As a result, the projection width w may be formed in a range of 0.1 μm to 10 μm.

Figure 6:
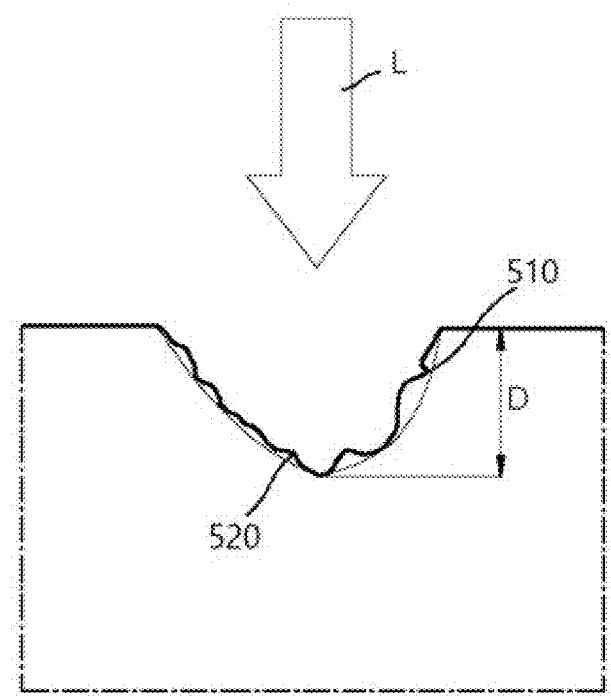
FIG. 6 is a diagram showing a cross section of a pattern according to an embodiment of the present invention.

FIG. 6 is a diagram showing a cross section of a pattern according to an embodiment of the present invention.

Referring to FIG. 6, a laser is irradiated in a laser irradiation direction L, and the processing groove 101 may be formed in the intraocular lens 100. The ridges 11 and 12 may be formed on both sides of the groove while the grooves 21 and 22 are formed. That is, the grooves 21 and 22 formed to be open between the adjacent ridges 11 and 12 may be formed to have predetermined depths D1 and D2. The grooves 21 and 22 may be provided with finer processing projections 510 and 520 and grooves 21 and 22 which will be described later with reference to the drawings to be more intuitively shown in the following drawings.

On the other hand, when the laser is irradiated in the laser irradiation direction L, the grooves 21 and 22 may be formed in the intraocular lens 100. Therefore, the grooves 21 and 22 may be formed in an intaglio shape by a predetermined depth, which may be formed in the shapes of a groove, a non-through hole, a drain, or the like. Here, the predetermined depth may be determined according to laser irradiation conditions and the material of the intraocular lens 100. For example, the laser irradiation conditions may include a laser output, a frequency of the laser, the irradiation time of the laser and the like.

Specifically, when the laser is irradiated to the intraocular lens 100 to form the grooves 21 and 22 by the predetermined depths, the processing groove 101 may not be formed by the depth by one-time irradiation. That is, as the laser output is higher, the predetermined depth may be formed within a shorter time. Of course, when processing with the high-output laser through a small number of times of irradiation, thermal deformation may occur depending on the material of the intraocular lens 100, and the possibility that the intraocular lens 100 may be damaged by the laser may be increased. Of course, the surfaces of the grooves 21 and 22 processed by the high-output laser may be formed to have roughness larger than that of the surfaces of the grooves 21 and 22 processed by a low-output laser many times.

Here, the processing by laser irradiation twice or more means that the depth of the laser irradiation is deeper than the depth that may be formed by one-time laser irradiation. To this end, the area irradiated by the laser onto a first object 100 may overlap. As a method of irradiating a laser so that the laser is overlapped in a first object 100, a method of irradiating two or more laser beams to a portion of a first object 100 with a time interval may be used. On the other hand, the ratio at which the laser overlaps may be referred to as an overlap ratio.

A spot size, a frequency, a scan interval, and a scanning speed of the laser to be irradiated may be factors that determine the overlap ratio of the laser, and the predetermined depth may be determined by the overlap ratio. For example, the longer the period of the frequency and the shorter the irradiation time, the lower the overlap ratio. Conversely, the shorter the period of the frequency and the longer the irradiation time, the higher the overlap ratio. Here, the high overlap ratio means that the specific gravity of the amount of energy emitted from the laser is increased per unit area, such that the frequency and the irradiation time of the laser may be selectively determined so that the laser may reach the predetermined depth.

Therefore, the depths of the grooves 21 and 22 formed by the laser irradiation are factors which may be selectively determined in consideration of conditions such as the material of the intraocular lens 100, the laser frequency, the scanning speed of the laser, the laser output and the like, and the grooves 21 and 22 and the processing projection 520 described in the present invention may also be determined according to the above-described conditions.

Figure 8A:
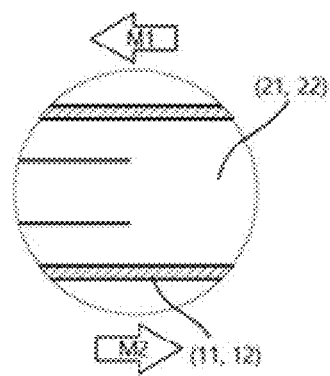
FIGS. 8A-8C are diagrams showing that positions and shapes of a boundary portion according to embodiments of the present invention are formed differently, respectively.
Figure 8B:
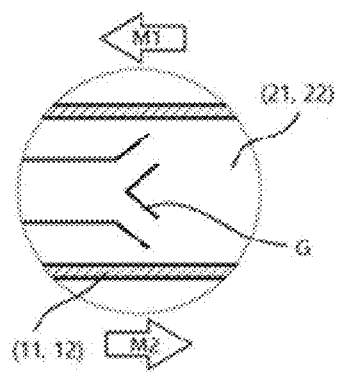
Figure 8C:
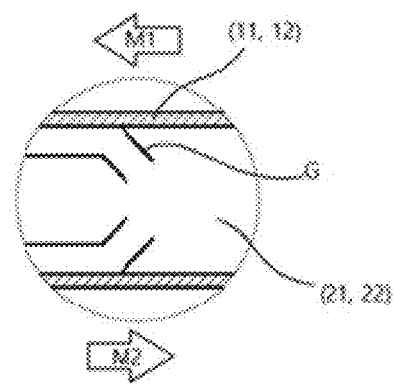
Figure 9:
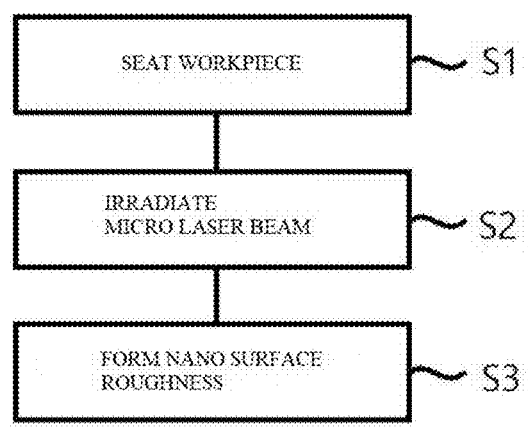
FIG. 9 is a flowchart showing a method of manufacturing an intraocular lens according to an embodiment of the present invention.

FIGS. 8A-8C are diagrams showing that locations and shapes of a boundary portion G according to embodiments of the present invention are formed differently, respectively.

Referring to FIG. 8A, a structure that becomes narrower from a front side toward a rear side based on a migration direction M1 of cells may be formed. Specifically, in the entire width, a cell migration path is formed in which the cross-sectional area through which cells migrate is reduced to ½, ⅓, or the like, such that the migration speed of cells may be increased. Such a structure may be included in a section in which the first pattern A and the second pattern B described above are continuously formed. Here, the portion where the cross-sectional area through which cells pass is narrow corresponds to the first pattern A, and the portion where the cross-sectional area through which cells pass is wide corresponds to the second pattern B. Unlike those described above, a migration direction may be an opposite migration direction M2.

In the case of the opposite migration direction, it may be applied to a section for lowering the migration speed, which may be formed the boundary that migrates from the optic portions 110, 210, 310, and 410 to the haptic portion 120, 220, 320, and 420 or any point on the haptic portions 120, 220, 320, and 420. Any point may be a point at which the second pattern B is formed.

Referring to FIG. 8B, the boundary portion G may be formed while decreasing the cross-sectional area through which the cells pass. Specifically, the boundary portion G may be configured to block the migration of cells in one direction M1 and bypass cells in the other direction M2 which is the opposite direction. The present embodiment also corresponds to the case where the cross-sectional area through which cells pass becomes narrower on the rear side and wider on the front side with respect to a traveling direction of cells. Of course, the narrow portion may be the portion of the first pattern A and the wide portion may be the portion of the second pattern B. The structure of the boundary portion G may also function as the structure for inhibiting the migration when cells migrate along the migration direction M1.

With the similar structure, referring to FIG. 8C, the cross-sectional area through which cells pass may be reduced to, for example, ⅓ on the rear side based on the migration direction M1 of cells. The boundary portion formed in the oblique direction with respect to the migration direction M1 of the cell may be positioned at a starting point of the point where the cross-sectional area through which cells pass is reduced. The boundary portion G may obliquely extend toward the front side of the migration direction from the side portions of the grooves 21 and 22, and the cells may be inhibited or retarded by the boundary portion G during the migration due to the structure. Unlike the case described above, in the opposite migration direction M2, the boundary portion G may serve to prevent cells from migrating in the reverse direction.

In the case of the opposite migration direction M2, it may be applied to a section for lowering the migration speed, which may be formed the boundary that migrates from the optic portions 110, 210, 310, and 410 to the haptic portion 120, 220, 320, and 420 or any points on the haptic portions 120, 220, 320, and 420. Any point may be a point at which the second pattern B is formed.

Meanwhile, as described above, the nano-sized surface roughness may be formed on the intraocular lenses 100, 200, 300, and 400 as seating (S1) of a workpiece and irradiation S2 of a micro laser beam are sequentially performed on the intraocular lenses 100, 200, 300, and 400. The workpiece may be the intraocular lens 100, 200, 300, 400, and 500 before the predetermined pattern is processed. The workpiece may include the haptic portions 110, 210, 310, and 410 having a circular shape from one side thereof and at least one optic portions 110, 210, 310, and 410 extending from the outer circumferential edge of the haptic portions 120, 220, 320, and 420. The workpiece is seated on the seat portion (not shown), and the micro-sized laser beam may be irradiated to the haptic portion 120, 220, 320, and 420 and the optic portion 110, 210, 310, and 410. The groove of the pattern formed by the micro-sized laser beam may serve to guide cells. The guide means controlling the direction, speed, and the like.

It is possible to increase the surface roughness of the groove included in the predetermined pattern by forming the structure having the surface roughness of nano units in the predetermined pattern formed by the micro-sized laser beam. The increased surface roughness of the groove means the roughness of the surface formed to be more rough than the surface of the groove processed by the micro-sized laser beam by forming a nano-sized irregular surface structure on the bottom and side surfaces of the groove formed by the formation of the groove, so that the surface roughness retards or inhibit the migration of cells. Therefore, the rough surface may be selectively provided only in a section in which cells are moved at a relatively low rate in controlling the migration speed of cells and may be formed in the pattern as a whole and in the region of the second pattern B with higher roughness.

A predetermined pattern may be a pattern in which the width of the groove of the first pattern A formed on the optic portions 110, 210, 310, and 410 is formed to be narrower than that of the groove of the second pattern B formed on at least a part of the haptic portions 120, 220, 320, and 420, and the predetermined pattern may be formed to be guided to the outer circumferential edges of the haptic portions 120, 220, 320, and 420 or the optic portions 110, 210, 310, and 410 so that the cell is away from the center of the optic portions 110, 210, 310, and 410. The boundary portion G described above can also be formed in a micro size through the irradiation of the laser beam.

Although the representative embodiments of the present invention have been disclosed in detail, those having ordinary skill in the field of technology to which the present invention pertains would understand that various modifications are possible, without departing from the scope of the present invention. Accordingly, the scope of the present invention should not be construed as being limited to the described embodiments but be defined by the appended claims as well as equivalents thereof.

What is claimed is:
1. An intraocular lens (IOL), comprising:
an optic portion having a circular shape and including a first pattern which includes a plurality of ridges and a plurality of grooves; and
a plurality of haptic portions extending from an outer circumferential edge of the optic portion and each including a second pattern which includes a plurality of ridges and a plurality of grooves,
wherein at least one of the ridges included in the first pattern and the second pattern and at least one of the grooves included in the first pattern and the second pattern includes a section in which a width is formed differently,
wherein the widths of the grooves of the second pattern in a haptic portion of the plurality of haptic portions is wider than the widths of the grooves of the first pattern in the optic portion,
wherein a groove of at least one of the first and second patterns includes a rugged part of nanometer units formed on a bottom surface thereof and a plurality of nano-sized projections formed on a side surface thereof,
wherein the first pattern is formed over the haptic portions and the optic portion, and the second pattern is formed only on the haptic portions.
2. The intraocular lens of claim 1, wherein a width ratio of the ridge and the groove included in the first pattern and the second pattern is formed within a range of 1:2 to 1:8.
3. The intraocular lens of claim 2, wherein a pattern in which the width of the ridge is 5 micrometers and the width of the groove is 30 micrometers is included in one of the first and second patterns.
4. The intraocular lens of claim 1, wherein the groove of at least one of the first and second patterns includes a boundary portion which retards or blocks migration of a cell.
5. The intraocular lens of claim 4, wherein the boundary portion forms a plurality of cell migration paths within the width of the groove to change a migration speed of the cell.
6. The intraocular lens of claim 4, wherein the boundary portion obliquely extend inward from a side wall of the groove to narrow a cross sectional area through which the cell passes in a forward direction in which the cell migrates and blocks the migration of the cell in a reverse direction to guide the migration direction of the cell.
7. The intraocular lens of claim 4, wherein the boundary portion is formed to protrude upward from a bottom surface of the groove and obliquely extends to bypass and block the migration of the cell in a forward direction in which the cell migrates and increase the cross sectional area through which the cell passes in a reverse direction.

8. The intraocular lens of claim 1, wherein each of the plurality of nano-sized projections is inclined in an oblique, downward direction from the side surface.

* * * * *